United States Patent
Wang

(10) Patent No.: US 9,918,478 B2
(45) Date of Patent: *Mar. 20, 2018

(54) WATER SOLUBLE ANTIMICROBIAL POLYACRYLATE SILVER SALT

(71) Applicant: Shyh Yeu Wang, Taoyuan (TW)

(72) Inventor: Shyh Yeu Wang, Taoyuan (TW)

(*) Notice: Subject to any disclaimer, the term of this patent is extended or adjusted under 35 U.S.C. 154(b) by 0 days.

This patent is subject to a terminal disclaimer.

(21) Appl. No.: 15/097,653

(22) Filed: Apr. 13, 2016

(65) Prior Publication Data

US 2016/0309721 A1    Oct. 27, 2016

(30) Foreign Application Priority Data

Apr. 21, 2015 (TW) .............................. 104112626 A

(51) Int. Cl.

| | | |
|---|---|---|
| *C08F 22/02* | (2006.01) | |
| *C08L 33/02* | (2006.01) | |
| *A01N 59/16* | (2006.01) | |
| *A61K 31/74* | (2006.01) | |
| *C08F 122/02* | (2006.01) | |
| *C08F 222/02* | (2006.01) | |

(52) U.S. Cl.
CPC .............. *A01N 59/16* (2013.01); *A61K 31/74* (2013.01); *C08F 22/02* (2013.01); *C08F 122/02* (2013.01); *C08F 222/02* (2013.01); *C08L 33/02* (2013.01)

(58) Field of Classification Search
CPC ...... C08F 22/02; C08F 122/02; C08F 222/02; C08L 33/02; A01N 59/16; A61K 31/74
See application file for complete search history.

(56) References Cited

U.S. PATENT DOCUMENTS

| | | | |
|---|---|---|---|
| 2,045,080 A | | 6/1935 | Hagedorn |
| 3,507,840 A | * | 4/1970 | Hurlock ............... B01D 3/36 203/12 |
| 5,709,870 A | | 1/1998 | Yoshimura et al. |

FOREIGN PATENT DOCUMENTS

| | | |
|---|---|---|
| CN | 101812240 A | 8/2010 |
| EP | 0710877 B1 | 5/2001 |
| EP | 1069468 B1 | 11/2006 |
| GB | 420533 A | 12/1934 |
| RU | 2220982 C2 | 1/2004 |

OTHER PUBLICATIONS https://en.wikipedia.org/wiki/Solubility_table; 2017.*
https://en.wikipedia.org/wiki/Solubility; 2017.*

* cited by examiner

*Primary Examiner* — Roberto Rabago
(74) *Attorney, Agent, or Firm* — Rosenberg, Klein & Lee

(57) ABSTRACT

This invention is about a water soluble antimicrobial polyacrylate silver salt. The molecular chain of the polyacrylate silver salt comprises sodium carboxylic group (—COONa) and silver carboxylic group (—COOAg). It is synthesized by dissolving an polyacrylate polymer comprising sodium carboxylic group (—COONa) in water and then exchanging the sodium carboxylic group of the polyacrylate polymer to silver carboxylic group (—COOAg) using silver salt in aqueous solution. Ultrafiltration membrane is used to remove the sodium salt generated from the metal ion exchanging procedure. An aqueous solution of water soluble antimicrobial polyacrylate silver salt with very few impurity is obtained. The water soluble antimicrobial polyacrylate silver salt is then obtain-ned from the aqueous solution. The molar ratio of —COOAg to —COONa of thus obtained water soluble antimicrobial polyacrylate silver salt can be as high as 66/34.

4 Claims, No Drawings

WATER SOLUBLE ANTIMICROBIAL POLYACRYLATE SILVER SALT

FIELD OF THE INVENTION

This invention is about a water soluble antimicrobial polyacrylate silver salt. The molecular chain of the polyacrylate silver salt comprises sodium carboxylic group (—COONa) and silver carboxylic group (—COOAg).

BACKGROUND OF THE INVENTION

Bacteria have big influence on human's daily life. They affect human health and cause illness and death. So, it is very important to fight against bacteria. Until now, most of the antimicrobial agents fighting bacteria are small molecule chemicals. They are used in many applications such as anti-bacterial hygiene products, food preservative . . . etc. They can also be used as water or soil sterilization. Small molecule antibacterial agents have inherent problems such as residual toxicity to the environment, the short-term antimicrobial effect, easy to be absorbed by the human body . . . etc. One way to solve these problems is to use antimicrobial polymer instead of small molecule antimicrobial agent.

The use of antimicrobial polymers offers promise for enhancing the efficacy of some existing antimicrobial agents and minimizing the environmental problems accompanying conventional antimicrobial agents by reducing the residual toxicity of the agents, increasing their efficiency and selectivity, and prolonging the lifetime of the antimicrobial agents. (quoted from Biomacromolecules, 2007, vol. 8, No. 5, page 1359-1384)

Since many antimicrobial applications are in aqueous or hydrophilic environment, such as preservatives for cosmetic, antibacterial hand sanitizer, antibacterial cleansers . . . etc. So there is a need for developing water-soluble antibacterial polymer.

Since ancient times, the antimicrobial effect of silver is well known and applied by human in their daily life. In early times, people made food container from silver because they found out that food or milk in silver container were preserved longer than in other kind of containers.

Till modern time, silver for antimicrobial application has extended to different forms such as silver ion and nano silver.

The antimicrobial silver ion is mostly existed in the form of salt such as silver nitrate, silver acetate and silver thiosulfate. However, most of the other salts of silver have low solubility in water.

Other than the salts mentioned above, silver ion can also form complex with organic molecule. The most famous one is silver sulfadiazine. It is widely used in treating burning wound. However, silver sulfadiazine, like most of the silver salt, has low solubility in water.

All the antimicrobial silver salts and antimicrobial organic complex mentioned above are still small molecules. They have all the drawbacks of antimicrobial small molecules. In order to combined the good antimicrobial property of silver ion and the benefit of polymer, the development of water soluble antimicrobial polymeric silver salt is very necessary.

Silver ion can be complexed with polymer to form polymeric silver salt. The polymeric silver salt has the same problem of low solubility in water. British patent GB420533 (A) disclose the preparation method of silver polyacrylic acid. Although the raw material, sodium polyacrylic acid, is soluble in water, the silver polyacrylic acid product cannot be dissolved in water. The objective of GB420533 (A) is to use silver polyacrylic acid as a general plastic material instead of antimicrobial polymer.

U.S. Pat. No. 5,709,870 discloses a water soluble silver containing antimicrobial carboxymethylcellulose (CMC). The preparation is done by suspending sodium CMC in water and exchange sodium with silver using silver nitrate. However, the silver content in polymer is lower than 1%.

In an article published in 2001(Pharmaceutical chemistry Journal, 2001, vol. 35, No 5, Page 252-253), a silver containing water soluble antimicrobial polyacrylic acid with chemical structure of $(CH_2CHCOOH)_n$—$(CH_2CHCOOAg)_m$ (n=9000~40000 and m=100~3000), the silver content between 4~10%) is presented. It is mentioned in the paper that the silver containing polyacrylic acid can be dissolved in water and has good antimicrobial property. However, in that paper, no preparation method is shown. Yet, in Russian patent RU2220982 filed by the same author, the preparation process is disclosed. The process includes steps of first mixing silver nitrate aqueous solution and polyacrylic acid aqueous solution together, stirring for 30 to 60 minutes and then drying at 50° C. to give a grey transparent product. It is obvious that no pure silver containing polyacrylic acid was separated and obtained by the preparation process of the Russian patent.

It is well know that among all the water soluble polymer, polyacrylate is the most versatile water soluble polymer. However, until now there is no water soluble antimicrobial polyacrylate silver salt been designed and synthesized so far.

SUMMARY OF THE INVENTION

This invention is about a water soluble antimicrobial polyacrylate silver salt. In order to obtained a polyacrylate silver salt with high silver content and good water solubility, this invention discloses a polyacrylate silver salt comprising both sodium carboxylic group (—COONa) and silver carboxylic group (—COO Ag). The high water solubility portion with sodium carboxylic group in the polyacrylate silver salt can compensate the low water solubility portion with silver carboxylic group in the same polyacrylate silver salt and makes the polyacrylate silver salt water soluble.

The water soluble antimicrobial polyacrylate silver salt of this invention can be synthesized by first doing metal ion exchange with silver salt in aqueous solution containing water soluble polyacrylate comprising sodium carboxylic group (—COONa). The sodium carboxylic group (—COONa) is changed to silver carboxylic group (—COOAg) by metal ion exchange with silver salt. The sodium salt byproduct produced in the metal ion exchange process is then removed by ultrafiltration membrane process to give an aqueous solution of polyacrylate silver salt. Finally, the water of the ultrafiltration treated aqueous solution of the polyacrylate silver salt is removed to give water soluble antimicrobial polyacrylate silver salt.

DETAILED DESCRIPTION OF THE INVENTION

Using silver salt to perform metal ion exchange with sodium carboxylic group to obtain silver carboxylic group has been well known for sometimes. EP0710877B1 and EP1069468B1 disclose some organic silver carboxylate compounds produced by metal ion exchange. Most of these organic silver carboxylate compounds are not soluble in water.

As mentioned above, the water soluble antimicrobial polyacrylate silver salt of this invention can be synthesized by metal ion exchange. The metal ion exchange is done by mixing water soluble polyacrylate comprising sodium carboxylic group with silver salt in aqueous solution and partially converting the sodium carboxylic group to silver carboxylic group to give a polyacrylate silver salt comprising two functional groups, sodium carboxylic group and silver carboxylic group. Although silver carboxylic group will make the polyacrylate silver salt insoluble in water, however with sodium carboxylic group presented in the same molecular chain of the polyacrylate silver salt, the polyacrylate silver salt can still be dissolved in water. In order for the polyacrylate to be soluble in water, the ratio of these two functional groups in the polyacrylate silver salt has to be carefully adjusted. Not enough sodium carboxylic group in the polyacrylate silver salt will make it insoluble in the water.

The aqueous solution after performing metal ion exchange contains water soluble antimicrobial polyacrylate salt, sodium nitrate and very small amount of possible remaining silver nitrate and small molecule impurities from raw material. The sodium nitrate and small molecule impurities have to be removed in order to get the pure water soluble antimicrobial polyacrylate salt. Conventional method of precipitation for polymer purification is not suitable in this case. The suitable non-solvents for precipitation have to be miscible with water and do not dissolve the polyacrylate silver salt of this invention. But these non-solvents such as acetone and methylethyl ketone are also worse solvent for sodium nitrate. So, when doing the precipitation, sodium nitrate will be precipitated out along with the polyacrylate silver salt. It is impossible to get pure polyacrylate silver salt using conventional precipitation method before the sodium nitrate is removed.

The method used to remove the sodium nitrate byproduct from metal ion exchange and small molecule impurities is ultrafiltration. Ultrafiltration is well known for selectively removing impurities by size exclusion. It is a simple and cost effective method to give aqueous solution of the water soluble antimicrobial polyacrylate silver salt with very few impurities.

After ultrafiltration treatment, the impurity of the aqueous solution of water soluble antimicrobial polyacrylate silver salt has been removed and the polyacrylate salt could be obtained by removing the water of the aqueous solution.

The water soluble polyacrylate comprising sodium carboxylic group can be sodium salt of polyacrylic acid, sodium salt of polymethacrylic acid, sodium salts of copolymer of acrylic acid and maleic acid, sodium salt of copolymer of methacrylic acid and maleic acid, sodium salt of copolymer of acrylic acid and methacrylic acid, sodium salt of copolymer of acrylic acid and other acrylic monomer or sodium salt of copolymer of methacrylic acid and other acrylic monomer.

The silver salt used for preparing the water soluble antimicrobial polyacrylate silver salt of this invention can be silver nitrate or silver acetate. The reason for using these two silver salts is because of their high solubility in water, more suppliers and lower cost than other silver salts. However, those silver salts with solubility higher than 0.0001 could also be used. It is just that the concentration of the aqueous solution for metal ion exchange has to be adjusted accordingly.

The metal ion exchange is carried out in aqueous solution. The water soluble polyacrylate comprising sodium carboxylic group is dissolved in water. The aqueous solution of silver salt is added into the solution with continuous stirring. If the addition speed is too fast during the addition of aqueous solution of silver salt, due to the local high concentration of silver salt at the addition site, there might be some white precipitate appeared. However, with continuous stirring, these white precipitate will eventually disappear and the solution will become clear. The maximum amount of silver salt that can be added is the amount at the point when these white precipitate stay undissolved for a certain period of time. The solution will show opaque appearance at this point. The maximum molar amount of silver salt will be less than the molar amount of sodium carboxylic group of the water soluble polyacrylate comprising sodium carboxylic group. It means that in order for the polyacrylate silver salt to stay soluble in water, there should be enough sodium carboxylic group in the polyacrylate silver salt. If the sodium carboxylic group in the polyacrylate silver salt is not enough, then the polyacrylate silver salt will not be water soluble.

Membranes with molecular weight cut off (MWCO) of 1000 to 1000000 could be used for ultrafiltration. The MWCO of the ultrafiltration membrane is better to be at least one order of magnitude smaller than the molecular weight of the water soluble polyacrylate comprising sodium carboxylic group used for the metal ion exchange. Such choose of MWCO can make sure that no polyacrylate silver salt will be removed along with the sodium nitrate during the ultrafiltration process.

The membrane could be sheet membrane or hollow fiber membrane. The module of the ultrafiltration membrane could be plate and frame module, spiral wound module or hollow fiber module.

The aqueous solution of polyacrylate silver salt obtained after metal ion exchange is put into a storage tank. Pure water can be added into the tank to dilute the solution. A pump is used to pump the aqueous solution of polyacrylate silver salt out from the storage tank into the ultrafiltration membrane module through the module inlet. The concentrated retentate solution of polyacrylate silver salt from the outlet of the ultrafiltration membrane module is fed back into the storage tank. The sodium nitrate and unwanted small molecule impurities will pass through the membrane to the permeate side and the polyacrylate silver salt will remain in the retentate side. The ultrafiltration process is kept going until the volume of aqueous solution of the polyacrylate silver salt in the storage tank is reduced to certain fraction of its original volume. Pure water is added into the storage tank to dilute the concentrated retentate solution of polyacrylate silver salt. Second ultrafiltration process is then carried out the same way as the first one. Such ultrafiltration operation is done multiple times until the sodium nitrate and small molecule impurities are removed to a negligible amount.

The last step is to obtain water soluble antimicrobial polyacrylate silver salt of this invention from its ultrafiltration purified aqueous solution. This could be done by conventional water removing process such as evaporation, evaporation at reduced pressure and spray drying. Water can also be removed by pouring the purified and concentrated aqueous solution of the polyacrylate silver salt into a nonsolvent. The precipitate is collected and dried to give the water soluble antimicrobial polyacrylate silver salt of this invention.

Determination of Metal Ion Exchange Ratio 500 cc pure water was put into a 1 liter flask with magnetic stirrer. 0.5 g of sodium salt of polyacrylic acid (molecular weight >8,000,000) was added into the flask. Stirring was started to dissolve the sodium salt of polyacrylic acid. The temperature of the solution was kept at 40° C. 1 g of 10% silver nitrate aqueous solution was added into the aqueous solution with continuous stirring. After 30 minutes, appearance of the aqueous solution was observed and recorded. Another 1 g of 10% silver nitrate was then added. After another 30 minutes, appearance of the aqueous solution was observed and recorded. Totally, 10 parts of 1 g of 10% silver nitrate were added into the aqueous solution. The 10 observation results of the appearance of the aqueous solution are shown at the following table.

found. It means that almost all the silver ion of silver nitrate added had been exchanged with sodium ion of the sodium salt of polyacrylic acid to give polyacrylic acid silver salt. All the polyacrylic acid silver salt obtained remained at the concentrated retentate solution.

The 1 liter concentrated retentate solution was diluted to 10 liters with pure water. The 10 liters of diluted solution was reduced to 1 liter by ultrafiltration again. Another dilution and ultrafiltration was done to give 1 liter of purified

TABLE 1

| | Number of addition of 1 g of 10% AgNO3 aqueous solution | | | | | | | | | |
|---|---|---|---|---|---|---|---|---|---|---|
| | 1 | 2 | 3 | 4 | 5 | 6 | 7 | 8 | 9 | 10 |
| Appearance of aqeuous solution of polyacrylic acid silver salt | clear | clear | clear | clear | clear | clear | opaque | opaque | opaque | opaque |
| Molar ratio of —COOAg/(—COOAg + —COONa) in polyacrylic acid silver salt | 0.111 | 0.221 | 0.332 | 0.443 | 0.554 | 0.664 | 0.775 | 0.886 | 0.996 | 1.000 |
| Weight percentage(%) of silver in polyacrylic acid silver salt | 11.5 | 21.2 | 29.3 | 36.3 | 42.3 | 47.6 | 52.3 | 56.5 | 60.2 | 60.2 |

From table 1, it can be seen that when the molar ratio of —COOAg/ (—COOAg+—COONa) is greater than 0.77, the polyacrylic acid silver salt obtain- ed will not be soluble in water. In order to make sure that the polyacrylic acid silver salt is soluble in water, the molar ratio of —COOAg/ (—COOAg+—COONa) is better to be lower than 0.66 or the weight ratio of silver of the poly- acrylic acid silver salt is better to be lower than 47%. The molar ratio of the silver carboxylic group to the sodium carboxylic group is more than 11/89 and less than 77/23.

EXAMPLE

Preparation of Polyacrylic Acid Silver Salt 10 g of sodium salt of polyacrylic acid was added into 2 liter pure water. High speed motor was used to dissolve the sodium salt of polyacrylic acid. The stirring speed was 10,000 rpm. The temperature was maintained at 40° C. A very viscous gel like transparent liquid was obtained after stirring for 3 minutes. 10 g of 50% silver nitrate aqueous solution was equally divided into 5 parts and added into the gel like liquid every 30 seconds under high speed stirring. After addition, the high speed stirring was continue for 5 minutes. The viscosity of the gel like liquid was greatly reduced. An aqueous solution of polyacrylic acid silver salt was obtained.

The aqueous solution of polyacrylic acid salt was diluted to 10 liters with pure water. A spiral wounded ultrafiltration module with diameter of 3 inches and length of 10 inches was used. The molecular weight cut off of this ultrafiltration module is 100,000. The volume of the diluted aqueous solution of polyacrylic acid silver salt was reduced to 1 liter. 100 cc of the permeate solution was collected. Sodium chloride was added. No silver chloride white precipitate was aqueous solution of polyacrylic acid silver salt with very few impurities.

10 cc of the concentrated retentate solution of polyacrylic acid silver salt was added into 1 liter of acetone. The precipitate was collected and dried to give purified polyacrylic acid silver salt. The polyacrylic acid silver salt can be dissolved into water again to give aqueous solution of the polyacrylic acid silver salt.

Antimicrobial Testing

An aqueous solution of polyacrylic acid silver salt obtained from the example above was prepared. The silver content of the aqueous solution was adjusted to 100 ppm. Two pieces of 1 cm$^2$ toasts were prepared. One was thoroughly wetted by spraying the aqueous solution of polyacrylic acid silver salt onto the toast. The other was also thoroughly wetted by spraying pure water onto the toast. These two pieces of wet toasts were stored in a humid environment at 30° C. The change of the toasts were observed and recorded every day. The results are shown at the following table.

TABLE 2

| | Observation Results | | | | | | |
|---|---|---|---|---|---|---|---|
| Day of experiment | day 1 | day 2 | day 3 | day 4 | day 5 | day 6 | day 7 |
| toast wetted with aqeous solution of polyacrylic acid silver salt | no mold | no mold | no mold | no mold | no mold | no mold | no mold |
| toast weetted with water | no mold | mold | mold | mold | mold | mold | mold |

It can be seen from the table above that the antimicrobial performance of the polyacrylic acid silver salt is very good. The toast wetted by aqueous solution of polyacrylic acid silver salt with silver content of 100 ppm showed no mold after staying at humid environment at 30° C. for 7 days.

What is claimed is:

1. A water soluble antimicrobial polyacrylate silver salt which forms a clear aqueous solution comprising a sodium carboxylic group and a silver carboxylic group in its molecular chain, a molar ratio of said silver carboxylic group to said sodium carboxylic group being more than 11/89 and less than 77/23.

2. The water soluble antimicrobial polyacrylate silver salt of claim 1, wherein the molar ratio of said silver carboxylic group to said sodium carboxylic group is less than 66/34.

3. A water soluble antimicrobial polyacrylic acid silver salt which forms a clear aqueous solution comprising a sodium carboxylic group and a silver carboxylic group in its molecular chain , a molar ratio of said silver carboxylic group to said sodium carboxylic group being more than 11/89 and less than 77/23.

4. The water soluble antimicrobial polyacrylic acid silver salt of claim 3, wherein the molar ratio of said silver carboxylic group to said sodium carboxylic group is less than 66/34.

* * * * *